(12) United States Patent
Leproust et al.

(10) Patent No.: US 9,580,746 B2
(45) Date of Patent: Feb. 28, 2017

(54) SYNTHESIS OF LONG FISH PROBES

(71) Applicant: Agilent Technologies, Inc., Loveland, CO (US)

(72) Inventors: Emily Marine Leproust, San Jose, CA (US); Siyuan Chen, San Jose, CA (US); Michael Ruvolo, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 288 days.

(21) Appl. No.: 14/146,216

(22) Filed: Jan. 2, 2014

(65) Prior Publication Data
US 2014/0256575 A1  Sep. 11, 2014

Related U.S. Application Data

(60) Provisional application No. 61/772,958, filed on Mar. 5, 2013.

(51) Int. Cl.
*C12Q 1/68* (2006.01)
*G06F 19/20* (2011.01)

(52) U.S. Cl.
CPC ......... *C12Q 1/6841* (2013.01); *C12Q 1/6883* (2013.01); *C12Q 1/6886* (2013.01); *G06F 19/20* (2013.01)

(58) Field of Classification Search
None
See application file for complete search history.

(56) References Cited

U.S. PATENT DOCUMENTS

| | | | |
|---|---|---|---|
| 8,034,917 B2 | 10/2011 | Yamada | |
| 2006/0008833 A1 | 1/2006 | Jacobson | |
| 2007/0238105 A1 | 10/2007 | Barrett et al. | |
| 2008/0057513 A1* | 3/2008 | Farrell | C12Q 1/6876 435/6.14 |
| 2011/0039735 A1 | 2/2011 | Yamada et al. | |
| 2012/0122159 A9 | 5/2012 | Li et al. | |

OTHER PUBLICATIONS

Ach, et al., "High resolution 1-15 fluorescence imaging of cellular DNA and RNA enabled by the synthesis of complex oligonucleotide libraries", AACR Meeting 2012 poster presentation.,2012, 1 page.
Rogan, et al., "Sequence-Based Design of Single-Copy Genomic DNA Probes for Fluorescence In Situ Hybridization", Genome Research., Cold Spring Harbor Laboratory Press. Woodbury. NY. US. vol. 11. No. 6. Jan. 2001, pp. 1086-1094.
Yamada, et al., "Visualization of fine-scale genomic structure by oligonucleotide-based high-resolution FISH", Cytogenet Genome Res, 2011, 132, No. 4. Jan. 2011, pp. 248-254.
EPO Communication for European application No. 14153591.4, mailed on Apr. 30, 2014, 7 pages.

* cited by examiner

*Primary Examiner* — David Thomas

(57) ABSTRACT

A method comprising: synthesizing a set of overlapping oligonucleotides that comprises probe sequences that hybridize to unique sequences in a chromosome, assembling the overlapping oligonucleotides in a way that produces one or more double stranded polynucleotides that each comprises multiple probe sequences, labeling the one or more double stranded polynucleotides to produce one or more labeled probes, and hybridizing the labeled probes to an intact chromosome, in situ, is provided.

13 Claims, 4 Drawing Sheets

US 9,580,746 B2

SYNTHESIS OF LONG FISH PROBES

This patent application claims the benefit of U.S. provisional application Ser. No. 61/772,958, filed on Mar. 5, 2013, all of which is incorporated by reference herein.

BACKGROUND

Chromosomal rearrangements, deletions, and other aberrations have long been associated with genetic diseases. Structural abnormalities in chromosomes often arise from errors in homologous recombination. Aneuploidy also referred to as numerical abnormality, in which the chromosome content of a cell is abnormal, may occur as a result of nondisjunction of chromosomes during meiosis. Trisomies, in which three copies of a chromosome are present instead of the usual two, are seen in Edwards, Patau and Down syndromes. Structural abnormalities and aneuploidy can occur in gametes and therefore will be present in all cells of an affected person's body, or they can occur during mitosis and give rise to a genetic mosaic individual who has some normal and some abnormal cells.

Genomic instability also leads to complex patterns of chromosomal rearrangements in certain cells, such as cancer cells, for example. Standard cytogenetic assays such as Giemsa (G) banding have identified numerous cancer-specific translocations and chromosomal abnormalities in cancer cells such as the Philadelphia (t9, 22) chromosome. Down syndrome (a trisomy), Jacobsen syndrome (a deletion) and Burkitt's lymphoma (a translocation) have traditionally been studied via karyotype analysis.

Improvements in cytogenetic banding and visualization such as M banding and spectral karyotyping (SKY) have enabled detailed analyses of inversions and translocations, as well as the identification of unbalanced gain or loss of chromosomal material in cancers of interest. Fluorescence in situ hybridization (FISH) further allows for the detection of the presence or absence of specific DNA sequences on chromosomes by using fluorescent probes that bind to only those parts of the chromosome with which they show a high degree of complementarity.

There is a large unmet need to develop technical methods that detect chromosomal abnormalities.

SUMMARY

A method comprising: a) synthesizing a set of overlapping oligonucleotides that comprises probe sequences that hybridize to unique sequences in a chromosome, b) assembling the overlapping oligonucleotides in a way that produces one or more double stranded polynucleotides that each comprises multiple probe sequences, c) labeling the one or more double stranded polynucleotides to produce one or more labeled probes, and d) hybridizing the labeled probes to an intact chromosome, in situ, is provided. The one or more double stranded polynucleotides may be made from the overlapping oligonucleotides in a variety of different ways, e.g., by ligation or by polymerase chain assembly, for example.

DEFINITIONS

Figure 1:
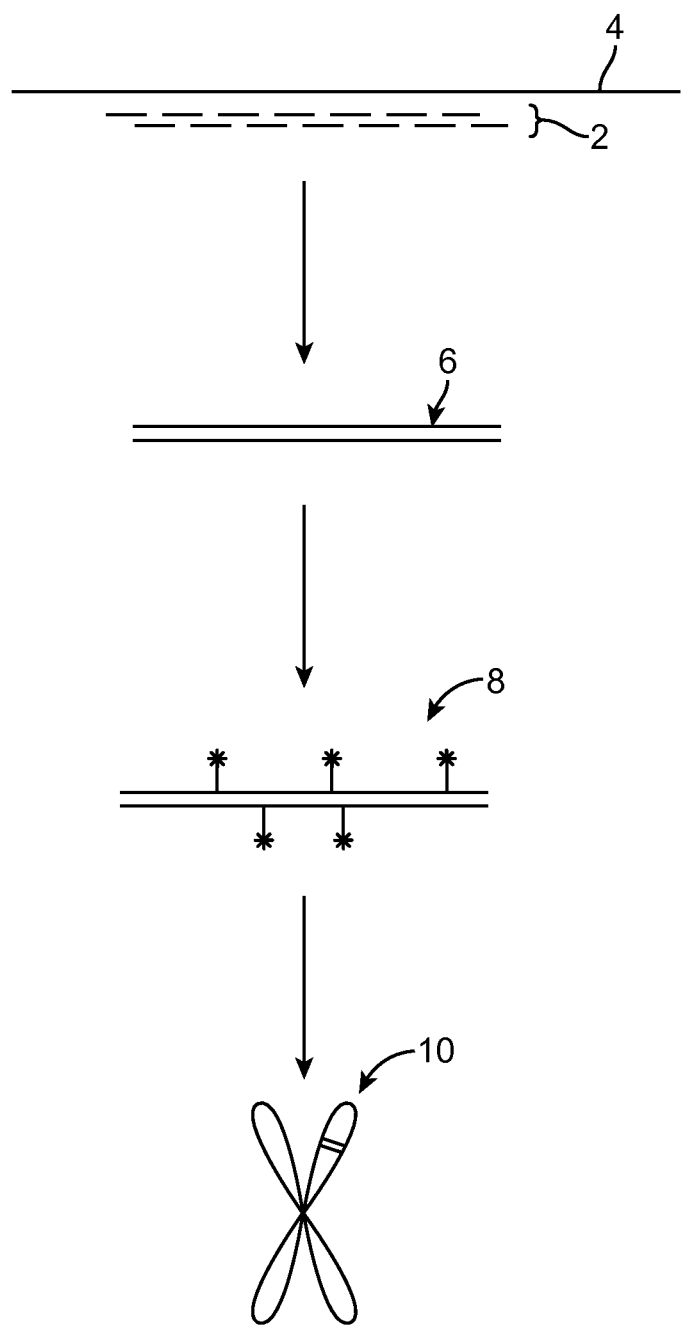
FIG. 1 schematically illustrates certain general features of the probe synthesis method described herein.

The term "sample" as used herein relates to a material or mixture of materials, typically, although not necessarily, in liquid form, containing one or more analytes of interest.

The term "genomic sample" as used herein relates to a material or mixture of materials, containing genetic material from an organism. The term "genomic DNA" as used herein refers to deoxyribonucleic acids that are obtained from an organism. The terms "genomic sample" and "genomic DNA" encompass genetic material that may have undergone amplification, purification, or fragmentation. The term "test genome," as used herein refers to genomic DNA that is of interest in a study.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "sequence-specific oligonucleotide" as used herein refers to an oligonucleotide that only binds to a single site in a haploid genome. In certain embodiments, a "sequence-specific" oligonucleotide may hybridize to a complementary nucleotide sequence that is unique in a sample under study.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is fully complementary to a target of interest such that every nucleotide in the sequence is complementary to every nucleotide in the target nucleic acid in the corresponding positions. In certain cases, a nucleotide sequence may be partially complementary to a target, in which not all nucleotide is complementary to every nucleotide in the target nucleic acid in all the corresponding positions.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence of the strand to hybridize therewith and thereby form the template for the synthesis of the extension product.

The term "probe," as used herein, refers to a nucleic acid that is partially or completely complementary to a nucleotide sequence of interest so as to stably hybridize thereto under stringent hybridization conditions. In certain cases, detection of a target analyte requires hybridization of a probe to a target. Probes may, but need not, have regions which are not complementary to a target sequence, as long as such sequences do not substantially alter the probe's desired specificity under stringent hybridization conditions. If such non-complementary regions exist they may contain a 5' promoter sequence and/or a binding site for RNA transcription, a restriction endonuclease recognition site, or may contain sequences which will confer a desired secondary or tertiary structure, such as a catalytic active site or a hairpin structure on the probe, on the target nucleic acid, or both. A probe may be labeled with a reporter group moiety such as a radioisotope, a fluorescent or chemiluminescent moiety, with an enzyme or other ligand, which can be used for detection or confirmation that the probe has hybridized to the target sequence. In certain embodiments, a probe may be immobilized on a surface of a substrate, where the substrate can have a variety of configurations, e.g., a sheet, bead, or other structure. In certain embodiments, a probe may be present on a surface of a planar support, e.g., in the form of an array.

The term "amplifying" as used herein refers to the process of synthesizing nucleic acid molecules that are complementary to one or both strands of a template nucleic acid. Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times (e.g., at least 5 or 10 times, up to 30 or 40 or more times) such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m = 81.5 + 16.6(\log_{10}[Na^+]) + 0.41$ (fraction G+C)−(60/N), where N is the chain length and [$Na^+$] is less than 1 M. See Sambrook and Russell (2001; Molecular Cloning: A Laboratory Manual, $3^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "chromosomal rearrangement," as used herein, refers to an event where one or more parts of a chromosome are rearranged within a single chromosome or between chromosomes. In certain cases, a chromosomal rearrangement may reflect an abnormality in chromosome structure. A chromosomal rearrangement may be an inversion, a deletion, an insertion or a translocation, for example.

The term "contacting" means to bring or put together. As such, a first item is contacted with a second item when the two items are brought or put together, e.g., by touching them to each other or combining them in the same solution. Thus, a "contacted sample" is a test chromosome onto which oligonucleotide probes have been hybridized.

The term "hybridization" refers to the specific binding of a nucleic acid to a complementary nucleic acid via Watson-Crick base pairing. Accordingly, the term "in situ hybridization" refers to specific binding of a nucleic acid to a metaphase or interphase chromosome.

The terms "hybridizing" and "binding", with respect to nucleic acids, are used interchangeably.

The terms "plurality", "set", "multiple" and "population" are used interchangeably to mean at least 2, at least 10, at least 100, at least 500, at least 1000, at least 10,000, at least 100,000, at least 1000,000, at least 10,000,000 or more.

The term "chromosomal region" as used herein denotes a contiguous length of nucleotides in a genome of an organism. A chromosomal region may be in the range of 10 kb in length to an entire chromosome, e.g., 100 kb to 10 MB for example.

A "test chromosome" is an intact metaphase or interphase chromosome isolated from a mammalian cell, where an intact chromosome has the same overall morphology as the same chromosome present in the mammalian cell, e.g., contains a centromere, a long arm containing a telomere and a short arm containing a telomere. A test chromosome may contain an inversion, translocation, deletion insertion, or other rearrangement relative to a reference chromosome. A test chromosome is the chromosome under study.

A "reference chromosome" is an intact metaphase chromosome to which a test chromosome may be compared to identify a rearrangement. A reference chromosome may be arbitrarily chosen. A reference chromosome may have a known sequence. A reference chromosome may itself contain a chromosomal rearrangement.

The term "reference chromosomal region," as used herein refers to a chromosomal region to which a test chromosomal region is compared. In certain cases, a reference chromosomal region may be of known nucleotide sequence, e.g., a chromosomal region whose sequence is deposited at NCBI's Genbank database or other database, for example.

The term "in situ hybridization conditions" as used herein refers to conditions that allow hybridization of a nucleic acid to a complementary nucleic acid in an intact chromosome. Suitable in situ hybridization conditions may include both hybridization conditions and optional wash conditions, which include temperature, concentration of denaturing reagents, salts, incubation time, etc. Such conditions are known in the art.

The term "distinct non-contiguous regions" refers to regions or intervals on a chromosome that are not contiguous.

The term "binding pattern" refers to the pattern of binding of a set of labeled probes to an intact chromosome.

The term "polymerase chain assembly", as used herein, refers to a protocol in which multiple overlapping oligonucleotides are combined and subjected to multiple rounds of primer extension (i.e., multiple successive cycles of primer extension, denaturation and renaturation in the presence of a polymerase and nucleotides) to extend the oligonucleotides using each other as a template, thereby producing a product molecule that contains the nucleotide sequences of each of the starting oligonucleotides. The product molecule is then amplified using primers that bind to sites at the ends of the product molecule prior to labeling.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins) In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired.) Nucleic acid may also be denatured chemically (e.g., using urea or NaOH).

The term "extending", as used herein, refers to the extension of a primer by the addition of nucleotides using a polymerase. If a primer that is annealed to a nucleic acid is extended, the nucleic acid acts as a template for extension reaction.

The term "overlapping oligonucleotides" refers to a set of oligonucleotides in which each oligonucleotide has an end (e.g., a 3' end) that is complementary to an end of another oligonucleotides of the set such that the ends of the overlapping oligonucleotides can hybridize to one another and be extended by a polymerase using the other oligonucleotide as a template.

The term "concatenating to one another" refers to joining to one another to make a element. Polynucleotide sequences can be concatenated to one another to produce a single sequence.

The term "repeat sequence" refers to a sequence in a genome that is not unique such as satellite DNA, LINES, SINES, and sequences that are otherwise found in at least two regions of a haploid genome, e.g., sequences found in homologous genes or genes that have been duplicated

DESCRIPTION OF EXEMPLARY EMBODIMENTS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Certain aspects of the subject method are illustrated in FIG. 1. In certain embodiments, the method comprises synthesizing a set of overlapping oligonucleotides 2 that comprises probe sequences that each hybridize to a unique sequence (i.e., to only one position) in a genome 4. In these embodiments, the overlapping oligonucleotides may be in the range of 50-200 nucleotides (or longer) in length. Each of the overlapping oligonucleotides has an end (e.g., a 3' end) that is complementary to an end of another of the overlapping oligonucleotides such that the ends of the overlapping oligonucleotides can hybridize to one another and, if necessary, be extended using another of the overlapping oligonucleotides as a template. There may be a 10% to 90% overlap between the adjacent oligonucleotides. In certain cases, the region of overlap (i.e., the region of complementarity between adjacent oligonucleotides) may be in the range of 12 to 50 bases, e.g., 15 to 30 bases. The probe sequence may be in the range of 10 to 200, e.g., 20 to 150 nucleotides, in length. Depending on how the oligonucleotides are made (e.g., depending on whether they are unprocessed oligonucleotides that have just been synthesized, or oligonucleotides that have been amplified by PCR, the oligonucleotides may be single stranded oligonucleotides or double stranded oligonucleotides. After the overlapping oligonucleotides have been made, the overlapping oligonucleotides are assembled in a way that produces one or more double stranded polynucleotides 6 that each comprises multiple (e.g., at least 2, at least 5, at least 10, at least 50 or at least 100 or more, up to 1,000 or more) probe sequences. As will be described in greater detail below, if the oligonucleotides are single stranded, the one or more double stranded polynucleotides may be made by polymerase chain assembly. In embodiments in which the oligonucleotides are double stranded, the one or more double stranded polynucleotides may be made by ligating the double stranded oligonucleotides together. After the one or more double stranded polynucleotides have been assembled, they are labeled to produce one or more labeled probes 8. The labeling may be done in any convenient way. For example, in certain cases, the probes may be labeled by chemically conjugating one or more labels to the one or more double stranded polynucleotides, e.g., using the Universal Linkage System (ULS™, KREATECH Diagnostics; van Gijlswijk et al Universal Linkage System: versatile nucleic acid labeling technique Expert Rev. Mol. Diagn. 2001 1:81-91). In brief, ULS™ labeling is based on the stable binding properties of platinum (II) to nucleic acids. The ULS molecule consists of a monofunctional platinum complex coupled to a detectable molecule of choice. Alternatively, the labeling may be done using nick translation, by random priming, or any other suitable method described in Ausubel, et al, (Short Protocols in Molecular Biology, 3rd ed., Wiley & Sons, 1995) or Sambrook, et al, (Molecular Cloning: A Laboratory Manual, Third Edition, (2001) Cold Spring Harbor, N.Y.). In certain cases, the one or more double stranded polynucleotides are labeled at multiple sites and not labeled by end labeling. The exemplary embodiment shown in FIG. 1 illustrates a probe that has been labeled by chemical conjugation. As would be apparent embodiments of the method that use other labeling methods (e.g., nick translation or random priming) will produce a product that is different to that illustrated in FIG. 1. After the one or more double stranded polynucleotides have been labeled, the resultant probes are hybridized to an intact chromosome, e.g., an intact metaphase or interphase chromosome isolated from a mammalian cell, in situ. Binding of the resultant probes to the intact chromosome should result in a binding pattern 10 that can be analyzed to potentially identify a chromosomal rearrangement.

As noted above, in certain embodiments the one or more double stranded polynucleotides may be assembled from overlapping single-stranded oligonucleotides by polymerase chain assembly, where as noted above, polymerase chain assembly involves subjecting multiple overlapping single stranded oligonucleotides to multiple rounds of primer extension (i.e., multiple successive cycles of primer extension, denaturation and renaturation in the presence of a polymerase and nucleotides) to extend the oligonucleotides using each other as a template, thereby producing a product molecule, and then amplifying the final product molecule using primers that bind to sites at the ends of the product molecule. Exemplary conditions for performing polymerase chain assembly methods are found in, e.g., Hughes, et al. (Methods in Enzymology 2011 498:277-309) and Wu, et al. (J. Biotechnol. (2006), 124:496-503), which are both incorporated by reference. If polymerase chain assembly is used, then the length of the product double stranded polynucleotide may be in the range of 100 bp to 5 kb, e.g., 200 bp to 3 kb. In these embodiments, the contiguous nucleotide sequences of the one or more double stranded polynucleotides produced by polymerase chain assembly may be at least 95% identical (e.g., at least 98% or at least 99% identical) to a sequence in a target chromosome. The overlapping ends of the oligonucleotides used in this method may be Tm-matched.

Figure 2:
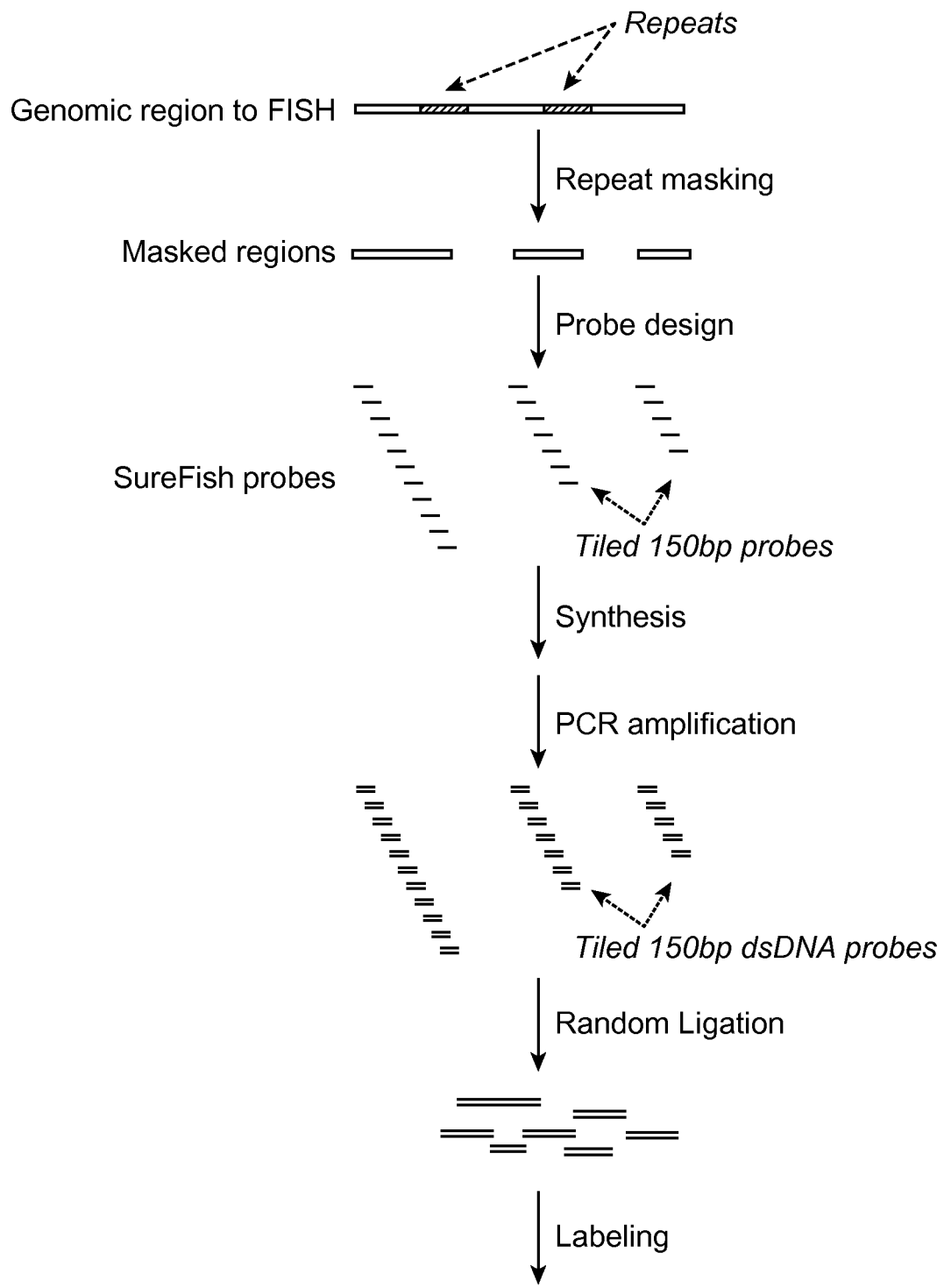
FIG. 2 schematically illustrates one embodiment of the method.

As noted above, the one or more double stranded polynucleotides may be assembled from overlapping double-stranded oligonucleotides by ligating the ends of the double-stranded oligonucleotides together. In these embodiments, the double-stranded oligonucleotides may be made by subjecting oligonucleotides PCR amplification, as described in, e.g., U.S. Pat. No. 8,034,917. In these cases, the double stranded oligonucleotides may be PCR amplified from a mixture of oligonucleotides, where the different oligonucleotides are of the following formula $X_1$-V-$X_2$ (from 5' to 3'), where $X_1$ and $X_2$ provide binding sites for a pair of PCR primers (e.g., where $X_1$ has the same sequence as a first PCR primer and $X_2$ has a sequence that is complementary to a second PCR primer), and V is a variable region that has a variable nucleotide sequence that is complementary a unique sequence in the genome. The variable regions, which generally correspond to a non-repeated region of a genome, can be amplified by a pair of PCR primers. In certain cases, the nucleotide sequences of $X_1$ and $X_2$ are the same for all of the oligonucleotides that are to be assembled such that all of the variable regions of a single set of oligonucleotides can be amplified with a single pair of PCR primers. In these embodiments, the PCR products $X_1$ and $X_2$ regions may contain sites for a Type IIS restriction enzyme, so that the $X_1$ and $X_2$ sequences can be removed from the PCR products to produce a set of overlapping double stranded oligonucleotides used in this embodiment of the method. Once produced, these double stranded oligonucleotides can be ligated together en masse, and labeled as described above. In these embodiments, the one or more double stranded polynucleotides are in the range of 300 to 5,000 base pairs in length, although, in certain embodiments, the length may be longer then 5,000 base pairs in length. Because this ligation is essentially random, the entire contiguous nucleotide sequence of the one or more double stranded polynucleotides may have less then 10% sequence identity to a sequence in a target chromosome. However, within the one or more double stranded polynucleotides made by this method there should be several shorter sequences (e.g., 50-150 nucleotides) that have at least 95% (e.g., at least 98% or at least 99%) sequence identity with the target sequence and that can hybridize to the target sequence. In these embodiments, the order of the probe sequences in the one or more double stranded polynucleotides is random. FIG. 2 illustrates one way in which this ligase-based embodiment can be performed.

Figure 3:
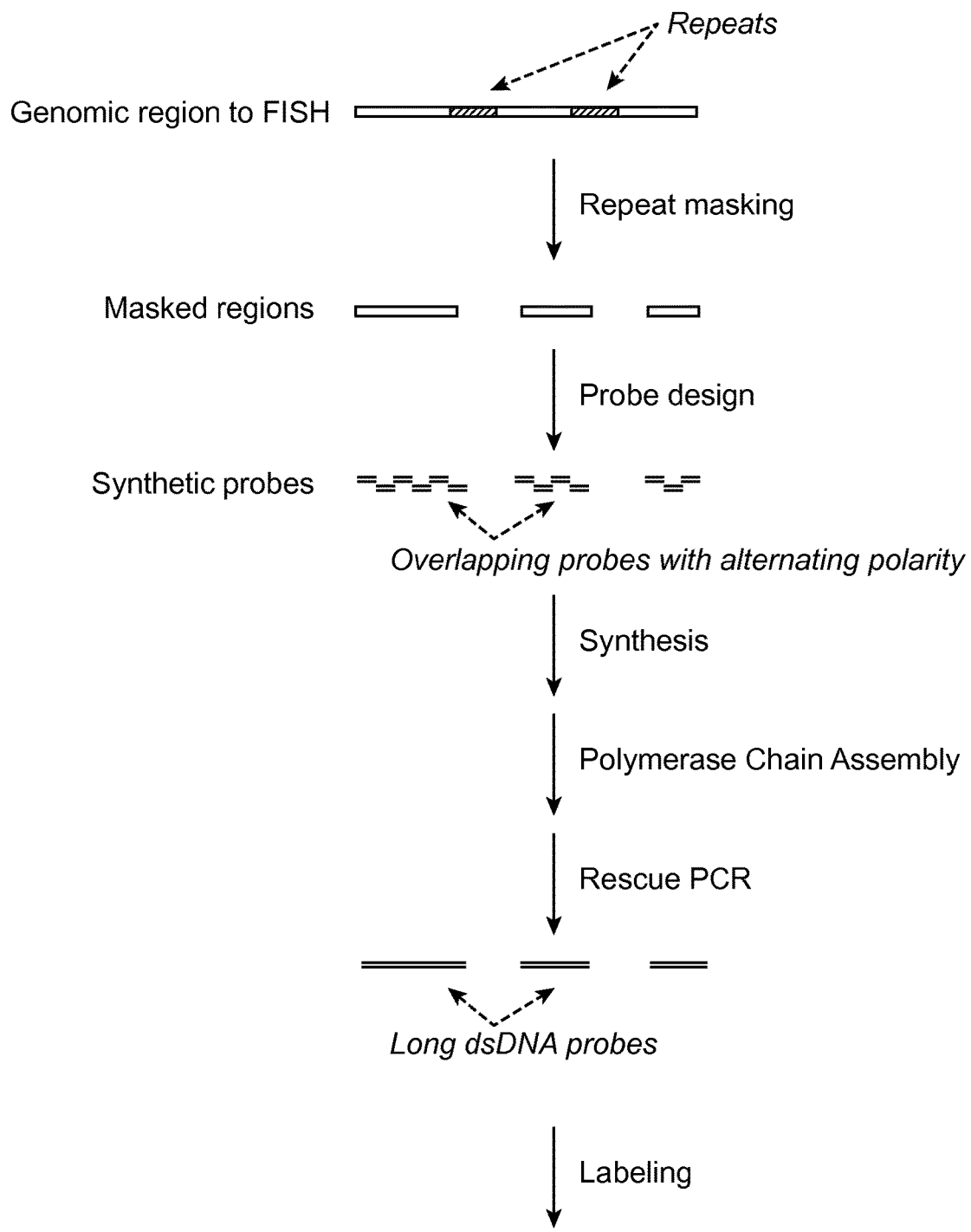
FIG. 3 schematically illustrates a further embodiment of the method.
Figure 4:
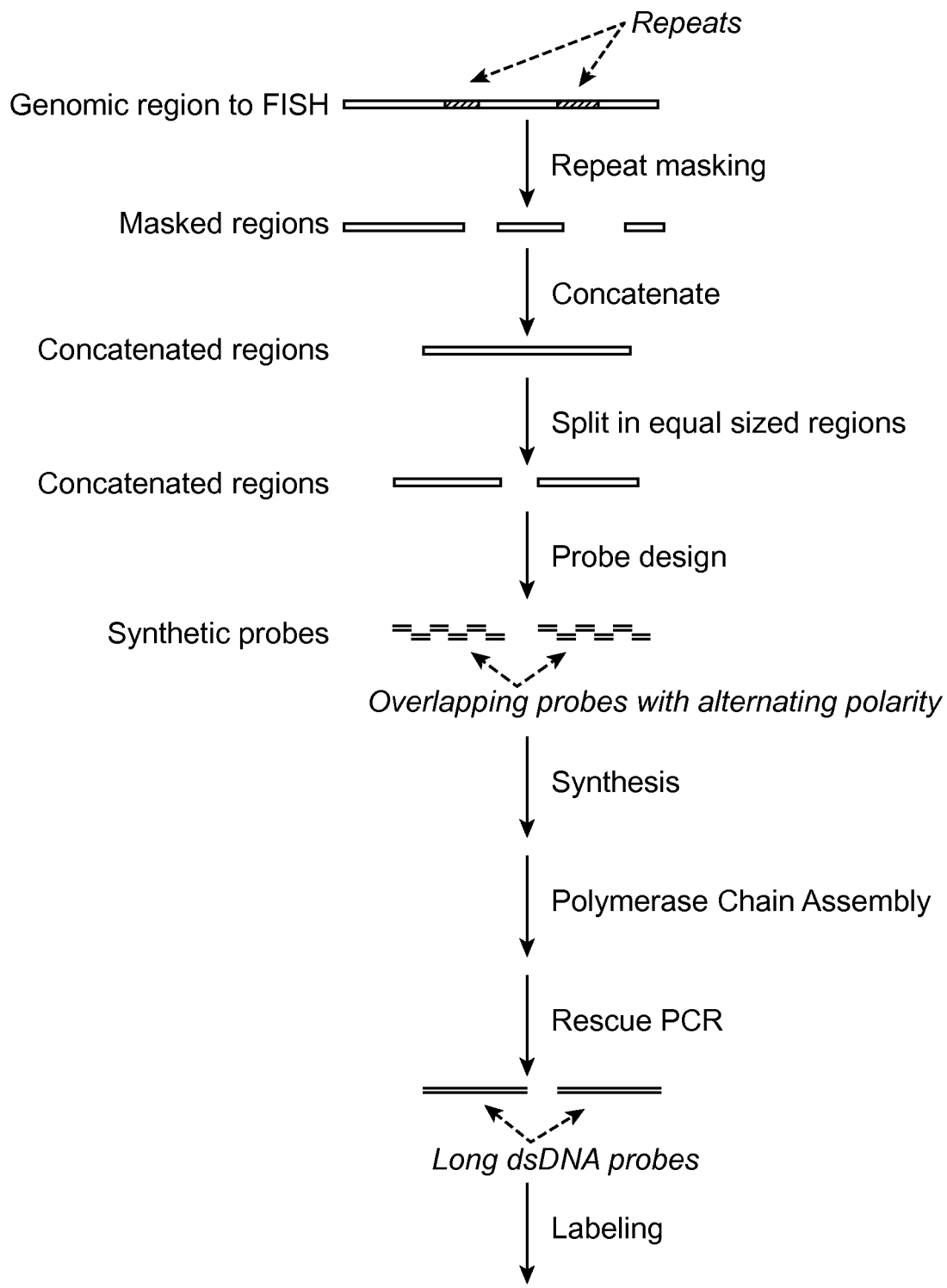
FIG. 4 schematically illustrates another embodiment of the method.

In some embodiments, the oligonucleotides hybridize to a plurality of distinct regions in a chromosome, wherein the distinct regions are separated by repeat sequences (e.g., sequences that are not unique in the genome such as satellite DNA, LINES, SINES, or sequences that are otherwise found in at least two parts of a genome such as those found in homologous genes and genes that have been duplicated). In these embodiments, the genomic sequence may be analyzed to identify target regions that are separated by repeat sequences. In certain cases, a set of overlapping probe sequences may be designed for each of the target regions. For example, if there are two, three or for target regions, then an equivalent number of double stranded polynucleotides can be produced, where each double stranded polynucleotide corresponds to a single target region. These embodiments may comprise designing a set of overlapping probe sequences for each of the target regions; synthesizing multiple sets of oligonucleotides that comprise the overlapping probe sequences; and assembling the overlapping probe sequences in a way that produces, for each of the target regions, a double stranded polynucleotide. This embodiment is schematically illustrated in FIG. 3 (where FIG. 3 illustrates a way in which this embodiment of the method can be done using polymerase chain assembly). In other cases, after target regions that are separated by repeated sequences have been identified, the nucleotide sequences may be concatenated to one another (i.e., joined to one another to make a single sequence containing each of the target sequences that may or may not be in the same order as they are found in the genome). In these embodiments, the concatenated nucleotide sequence may be split into multiple regions that are of defined length (e.g., a length in the range of 500 bp to 5 kb), and a set of probe sequences may be designed for each of the multiple regions. Consistent with the above, this method may involve synthesizing multiple sets of overlapping oligonucleotides that comprise the probe sequences; and assembling the probe sequences in a way that produces, for each of the multiple regions, a double stranded polynucleotide that can be labeled, as described above. FIG. 4 illustrates a way in which this embodiment of the method can be done by polymerase chain assembly.

As would be apparent, different double stranded polynucleotides corresponding to different regions in a genome can be labeled with the same label (e.g., the same fluorophore) and, in certain cases, different double stranded polynucleotides may combined prior to labeling. In certain cases, different double stranded polynucleotides may be labeled using different labels (e.g., different fluorophores).

In certain embodiments, the oligonucleotide used in the subject may be provided on an array. In certain embodiments, the array may be synthesized using in situ synthesis methods in which nucleotide monomers are sequentially added to a growing nucleotide chain that is attached to a solid support in the form of an array. Such in situ fabrication methods include those described in U.S. Pat. Nos. 5,449,754 and 6,180,351 as well as published PCT application no. WO 98/41531, the references cited therein, and in a variety of other publications. In one embodiment, the oligonucleotides used in the method may be made by fabricating an array of the oligonucleotides using in situ synthesis methods, and cleaving oligonucleotides from the array.

Fluorescent dyes (fluorophores) suitable for use as labels in the present method can be selected from any of the many dyes suitable for use in imaging applications. A large number of dyes are commercially available from a variety of sources, such as, for example, Molecular Probes (Eugene, Oreg.) and Exciton (Dayton, Ohio), that provide great flexibility in selecting a set of dyes having the desired spectral properties. Examples of fluorophores include, but are not limited to, 4-acetamido-4'-isothiocyanatostilbene-2,2' disulfonic acid; acridine and derivatives such as acridine, acridine orange, acridine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-amino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylaminolnaphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; Alexa-Fluor dyes (e.g., Alexa Fluor 350, Alexa Fluor 430, Alexa Fluor 488, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, Alexa Fluor 750), Pacific Blue, Pacific Orange, Cascade Blue, Cascade Yellow; Quantum Dot dyes (Quantum Dot Corporation); Dylight dyes from Pierce (Rockford, Ill.), including Dylight 800, Dylight 680, Dylight 649, Dylight 633, Dylight 549, Dylight 488, Dylight 405; or combinations thereof. Other fluorophores or combinations thereof known to those skilled in the art may also be used, for example those available from Molecular Probes (Eugene, Oreg.) and Exciton (Dayton, Ohio).

Table 1 below provides exemplary combinations of fluorophores that may be used together in combinations of 2, 3 or 4. This table is by no means comprehensive. In Table 1, 20 different 2 dye combinations, 9 different 3 dye combinations, and 8 different 4 dye combinations are denoted (read vertically; filled-in black box indicates dyes in the combination).

TABLE 1

Exemplary Dye Combinations.

| Fluorophore | 2 Dyes | 3 Dyes | 4 Dyes |
|---|---|---|---|
| Pacific Blue | | | |
| Pacific Orange | | | |
| AF 350 | | | |
| AF 488 (FITC) | | | |
| AF 594 | | | |
| AF 647 (Cy5) | | | |
| AF 700 (Cy5.5) | | | |
| AF 750 (Cy7) | | | |

(AF = Alexa Fluor)

Method for Sample Analysis

Probes made by the method described above may be hybridized to a sample containing intact chromosomes, and binding of the probes is analyzed. For example, an interphase or metaphase chromosome preparation may be produced. The chromosomes are attached to a substrate, e.g., glass and contacted with the probe and incubated under hybridization conditions. Wash steps remove all unhybridized or partially-hybridized probes, and the results are visualized and quantified using a microscope that is capable of exciting the dye and recording images. Such methods are generally known in the art and may be readily adapted for use herein. For example, the following references discuss chromosome hybridization: Ried et al., Human Molecular Genetics, Vol 7, 1619-1626; Speicher et al, Nature Genetics, 12, 368-376, 1996; Schröck et al., Science, 494-497, 1996; Griffin et al., Cytogenet Genome Res. 2007; 118(2-4):148-56; Peschka et al., Prenat Diagn., 1999, December; 19(12): 1143-9; Hilgenfeld et al, Curr Top Microbiol Immunol., 1999, 246: 169-74.

Prior to in situ hybridization, the probes may be denatured. Denaturation is typically performed by incubating in the presence of high pH, heat (e.g., temperatures from about 70° C. to about 95° C.), organic solvents such as formamide and tetraalkylammonium halides, or combinations thereof.

Intact chromosomes are contacted with labeled probes under in situ hybridizing conditions. "In situ hybridizing conditions" are conditions that facilitate annealing between a nucleic aid and the complementary nucleic acid in the intact chromosomes. Hybridization conditions vary, depending on the concentrations, base compositions, complexities, and lengths of the probes, as well as salt concentrations, temperatures, and length of incubation. For example, in situ hybridizations may be performed in hybridization buffer containing 1×-2×SSC, 50% formamide, and blocking DNA to suppress non-specific hybridization. In general, hybridization conditions include temperatures of about 25° C. to about 55° C., and incubation times of about 0.5 hours to about 96 hours. Suitable hybridization conditions for a set of oligonucleotides and chromosomal target can be determined via experimentation which is routine for one of skill in the art.

Fluorescence of a hybridized chromosome can be evaluated using a fluorescent microscope. In general, excitation radiation, from an excitation source having a first wavelength, passes through excitation optics. The excitation optics causes the excitation radiation to excite the sample. In response, fluorescent molecules in the sample emit radiation that has a wavelength that is different from the excitation wavelength. Collection optics then collects the emission from the sample. The computer also can transform the data collected during the assay into another format for presentation. In general, known robotic systems and components can be used.

In certain embodiments, the signal from the binding of the labeled probe to a chromosome may be compared with that of a reference chromosome. The reference chromosome may be from a healthy or wild-type organism. Briefly, the method comprises contacting under in situ hybridization conditions a test chromosome from the cellular sample with a plurality of fluorescently-labeled FISH probes generated by the subject method and contacting under in situ hybridization conditions a reference chromosome with the same plurality of fluorescently-labeled FISH probes. After hybridization, the emission spectra created from the unique binding patterns from the test chromosome are compared against those of the reference chromosome.

Thus, the structure of a test chromosome may be determined by comparing the pattern of binding of the labeled FISH probes to the test chromosome with the binding pattern of the same labeled FISH probes with a reference chromosome. The binding pattern of the reference chromosome may be determined before, after or at the same time as the binding pattern for the test chromosome. This determination may be carried out either manually or in an automated system. The binding pattern associated with the test chromosome can be compared to the binding pattern that would be expect for known deletions, insertions, translocation, fragile sites and other more complex rearrangements, and/or refined breakpoints. The matching may be performed by using computer-based analysis software known in the art. Determination of identity may be done manually (e.g., by viewing the data and comparing the signatures by hand), automatically (e.g., by employing data analysis software configured specifically to match optically detectable signature), or a combination thereof.

In another embodiment, the test sample is from an organism suspected to have cancer and the reference sample may comprise a negative control (non-cancerous) representing wild-type genomes and second test sample (or a positive control) representing a cancer associated with a known chromosomal rearrangement. In this embodiment, comparison of all these samples with each other using the subject method may reveal not only if the test sample yields a result that is different from the wild-type genome but also if the test sample may have the same or similar genomic rearrangements as another cancer test sample.

Kits

Also provided by the subject invention is a kit for practicing the subject method, as described above. In certain cases, the subject kit contains a plurality of sets of overlapping oligonucleotide probes, as discussed above. The kit may further contain reagents for polymerase chain assembly, PCR of the oligonucleotides, ligase, reagents for fluorescent labeling of double stranded polynucleotides, reagents for in situ hybridization, and/or a reference sample to be employed in the subject method. The various components of the kit may be in separate vessels.

In addition to above-mentioned components, the subject kit may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject method finds use in a variety of applications, where such applications generally include genomic DNA analysis applications in which the presence of a particular chromosomal rearrangement in a given sample is to be detected. The subject methods may also be used to finely map chromosomal breakpoints, and other aberrations, such as micro-inversions, deletions and translocations in certain cases without a priori knowledge of their location.

In some embodiments, hybridizing of a set of the subject probes to a target chromosome can provide a multi-color pattern. The chromosome under study, which may or may not be suspected of containing a chromosomal rearrangement, is contacted with labeled probes. After hybridization, the binding pattern of the probes is analyzed, as described above.

Specific detection applications of interest include but are not limited to chromosomal rearrangements and aberrations. One embodiment of the genomic analysis assay allows the detection of a chromosome inversion. In this embodiment, the assay contacts probes specific for a region of a reference chromosomal region under in situ hybridization conditions. If the test chromosomal region contains an inverted chromosomal segment that is visualized by a specific alteration in the characteristic emission spectra, an inversion has occurred. Matching the location of a probe to a database may provide the nucleotide sequence information of the probe hybridized to the test chromosome. Using the sequence information, the detailed location of the inversion junction may be deciphered.

The subject methods also find utility in the detection of chromosomal rearrangements. In this embodiment, the assay contacts probes specific for a region of a reference chromosomal region under in situ hybridization conditions. If the test chromosomal region contains newly juxtaposed segments from distant chromosomal regions that are visualized by their characteristic emission spectra, a translocation or complex chromosomal aberration has occurred. In certain cases, sequence information from a database describing the starting probes can be used to decipher the location of the translocation junction.

The subject methods find use in a variety of diagnostic and research purposes since chromosomal inversions and translocations play an important role in conditions relevant to human diseases and genomic evolution of many organisms.

In particular, the above-described methods may be employed to diagnose, or investigate various types of genetic abnormalities, cancer or other mammalian diseases, including but not limited to, leukemia; breast carcinoma; prostate cancer; Alzheimer's disease; Parkinson's disease; epilepsy; amyotrophic lateral sclerosis; multiple sclerosis; stroke; autism; Cri du chat (truncation on the short arm on chromosome 5), 1p36 deletion syndrome (loss of part of the short arm of chromosome 1), Angelman syndrome (loss of part of the long arm of chromosome 15); Prader-Willi syndrome (loss of part of the short arm of chromosome 15); acute lymphoblastic leukemia and more specifically, chronic myelogenous leukemia (translocation between chromosomes 9 and 22); Velocardiofacial syndrome (loss of part of the long arm of chromosome 22); Turner syndrome (single X chromosome); Klinefelter syndrome (an extra X chromosome); Edwards syndrome (trisomy of chromosome 18); Down syndrome (trisomy of chromosome 21); Patau syndrome (trisomy of chromosome 13); and trisomies 8, 9 and 16, which generally do not survive to birth.

The disease may be genetically inherited (germline mutation) or sporadic (somatic mutation). Many exemplary chromosomal rearrangements discussed herein are associated with and are thought to be a factor in producing these disorders. Knowing the type and the location of the chromosomal rearrangement may greatly aid the diagnosis, prognosis, and understanding of various mammalian diseases.

The above-described methods can also be used to compare the genomes of two biological species in order to deduce evolutionary relationships.

Chromosomes may be isolated from a variety of sources, including tissue culture cells and mammalian subjects, e.g., human, primate, mouse or rat subjects. For example, chromosomes may be analyzed from less than five milliliters (mL) of peripheral blood. White blood cells contain chromosomes while red blood cells do not. Blood may be collected and combined with an anti-clotting agent such as sodium heparin. Chromosomes may also be analyzed from amniotic fluid, which contains fetal cells. Such cells can be grown in tissue culture so that dividing cells are available for chromosomal analysis within 5-10 days. Chromosomes may also be analyzed from bone marrow, which is useful for diagnosis of leukemia or other bone marrow cancers. Chromosomes may also be analyzed from solid tissue samples. A skin or other tissue biopsy in the range of about 2-3 mm may be obtained aseptically and transferred to a sterile vial containing sterile saline or tissue transport media to provide material for chromosome analysis. Fetal tissue obtained after a miscarriage can also be used for chromosome analysis, such as from the fetal side of the placenta, the periosteum overlying the sternum or fascia above the inguinal ligament, or from chorionic villi. Fetal tissue can also be collected from multiple sites such as the kidneys, thymus, lungs, diaphragm, muscles, tendons, and gonads. An amniocentesis may also be performed.

In addition to the above, the instant methods may also be performed on bone marrow smears, blood smears, paraffin embedded tissue preparations, enzymatically dissociated tissue samples, uncultured bone marrow, uncultured amniocytes and cytospin preparations, for example.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method comprising:
   (a) synthesizing a set of overlapping oligonucleotides that comprises probe sequences that hybridize to unique sequences in a chromosome;
   (b) assembling the overlapping oligonucleotides in a way that produces one or more double stranded polynucleotides that each comprises multiple probe sequences, wherein the contiguous nucleotide sequence of each of said one or more double stranded polynucleotides is at least 95% identical to a sequence of said chromosome;
   (c) labeling the one or more double stranded polynucleotides to produce one or more labeled probes; and
   (d) hybridizing said labeled probes to an intact chromosome that comprises repeat sequences, in situ.

2. The method of claim 1, wherein said assembling is done by ligating multiple double stranded oligonucleotides to one another.

3. The method of claim 1, wherein said assembling is done by polymerase chain assembly.

4. The method of claim 1, wherein said labeling is done by random priming.

5. The method of claim 1, wherein said labeling is done by nick translation.

6. The method of claim 1, wherein said labeling is done by conjugating one or more labels to said one or more double stranded polynucleotides.

7. The method of claim 1, wherein said probe sequences are in the range of 10-150 nucleotides in length.

8. The method of claim 1, wherein said one or more double stranded polynucleotides are in the range of 300 to 5,000 base pairs in length.

9. A method comprising:
   analyzing a genomic sequence to identify target regions that are separated by repeat sequences;
   designing a set of overlapping probe sequences for each of said target regions;
   synthesizing oligonucleotides that comprise said overlapping probe sequences; and
   assembling the overlapping probe sequences in a way that produces, for each of said target regions, a double stranded polynucleotide, wherein the contiguous nucleotide sequence of said double stranded polynucleotide for each of said target regions is at least 95% identical to the sequence of said target region.

10. The method of claim 1, wherein said chromosome is a mammalian chromosome.

11. The method of claim 1, further comprising:
    (e) reading the product of step (d) using a microscope to produce a hybridization pattern.

12. The method of claim 11, further comprising:
    (f) comparing said hybridization pattern to a control hybridization pattern.

13. The method of claim 12, wherein said comparing identifies a chromosomal rearrangement.

* * * * *

UNITED STATES PATENT AND TRADEMARK OFFICE
CERTIFICATE OF CORRECTION

PATENT NO. : 9,580,746 B2
APPLICATION NO. : 14/146216
DATED : February 28, 2017
INVENTOR(S) : Emily Marine Leproust et al.

Page 1 of 1

It is certified that error appears in the above-identified patent and that said Letters Patent is hereby corrected as shown below:

In the Specification

In Column 6, Line 30, delete "mins)" and insert -- mins). --, therefor.

In Column 6, Line 60, after "duplicated" insert -- . --.

In Column 9, Line 44, delete "then" and insert -- than --, therefor.

In Column 10, Lines 65-66, delete "-trifluoromethylcouluarin" and insert
-- -trifluoromethylcoumarin --, therefor.

In Column 11, Line 3, delete "-isothiocyanatophenyl" and insert -- -isothiocyanatophenyl) --, therefor.

In Column 11, Lines 6-7, delete "-[dimethylaminolnaphthalene" and
insert -- -[dimethylamino]naphthalene --, therefor.

In Columns 11-12, Line 9, delete "Combinations ." and insert -- Combinations --, therefor.

In Column 12, Line 54, delete "aid" and insert -- acid --, therefor.

Signed and Sealed this
Twenty-fifth Day of April, 2017

Michelle K. Lee
*Director of the United States Patent and Trademark Office*